(12) United States Patent
Ichihara et al.

(10) Patent No.: US 10,130,263 B2
(45) Date of Patent: Nov. 20, 2018

(54) PHOTOACOUSTIC MEASURING APPARATUS

(71) Applicant: CANON KABUSHIKI KAISHA, Tokyo (JP)

(72) Inventors: Shigeru Ichihara, Tokyo (JP); Yukio Furukawa, Sagamihara (JP); Shuichi Kobayashi, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/614,984

(22) Filed: Jun. 6, 2017

(65) Prior Publication Data

US 2017/0265752 A1 Sep. 21, 2017

Related U.S. Application Data

(62) Division of application No. 14/193,117, filed on Feb. 28, 2014, now Pat. No. 9,700,214, which is a division
(Continued)

(30) Foreign Application Priority Data

Jun. 10, 2010 (JP) ................................. 2010-132860

(51) Int. Cl.
*G01N 29/24* (2006.01)
*A61B 8/08* (2006.01)
(Continued)

(52) U.S. Cl.
CPC .......... *A61B 5/0095* (2013.01); *A61B 5/0091* (2013.01); *A61B 5/4312* (2013.01);
(Continued)

(58) Field of Classification Search
CPC ... A61B 5/0095; A61B 5/0091; A61B 5/4312; A61B 5/708; A61B 8/0825;
(Continued)

(56) References Cited

U.S. PATENT DOCUMENTS

| 6,212,421 B1 | 4/2001 | Vo-Dinh et al. .............. 600/407 |
| 2006/0184042 A1 | 8/2006 | Wang et al. .................. 600/476 |

(Continued)

FOREIGN PATENT DOCUMENTS

| JP | 2001-100146 | 4/2001 |
| JP | 2003-270585 | 9/2003 |
| JP | 2009-031268 | 2/2009 |

OTHER PUBLICATIONS

Office Action dated Jan. 7, 2014 in counterpart Japanese patent application 2010-132860, with translation.
(Continued)

*Primary Examiner* — Manish S Shah
*Assistant Examiner* — Rose M Miller
(74) *Attorney, Agent, or Firm* — Fitzpatrick, Cella, Harper & Scinto

(57) ABSTRACT

A photoacoustic measuring apparatus includes a light source, a movable holding unit which holds an object, a light diffusing unit which fixes the distance between the light diffusing unit and the holding unit and diffuses light incident from the light source, and an acoustic wave obtaining unit which obtains an acoustic wave generated from the object by the light emitted via the holding unit and the light diffusing unit.

8 Claims, 9 Drawing Sheets

Related U.S. Application Data of application No. 13/151,543, filed on Jun. 2, 2011, now abandoned.

(51) Int. Cl.
*A61B 5/00* (2006.01)
*G01N 21/17* (2006.01)

(52) U.S. Cl.
CPC ............ *A61B 5/708* (2013.01); *A61B 8/0825* (2013.01); *G01N 21/1702* (2013.01); *G01N 29/2418* (2013.01); *G01N 2021/1787* (2013.01); *G01N 2201/0634* (2013.01)

(58) Field of Classification Search
CPC ........... G01N 21/1702; G01N 21/1708; G01N 2201/0634; G01N 29/2418
USPC .................................. 73/643, 584; 600/459
See application file for complete search history.

(56) References Cited

U.S. PATENT DOCUMENTS

| | | | |
|---|---|---|---|
| 2009/0005685 A1 | 1/2009 | Nagae et al. | 600/459 |
| 2010/0058870 A1 | 3/2010 | Kobayashi | 73/596 |
| 2010/0094134 A1 | 4/2010 | Zhu et al. | 600/473 |
| 2010/0319453 A1 | 12/2010 | Ichihara et al. | 73/596 |
| 2011/0102797 A1 | 5/2011 | Ichihara et al. | 356/445 |
| 2011/0270071 A1 | 11/2011 | Furukawa | 600/437 |
| 2013/0006090 A1 | 1/2013 | Miyasato | 600/407 |

OTHER PUBLICATIONS

Office Action dated Feb. 3, 2015 in counterpart Japanese patent application 2014-046176, with translation.

PHOTOACOUSTIC MEASURING APPARATUS

RELATED APPLICATIONS

This application is a divisional of application Ser. No. 14/193,117, filed Feb. 28, 2014, which is a divisional of application Ser. No. 13/151,543, filed Jun. 2, 2011, claims benefit of the filing dates of those applications under 35 U.S.C. § 120, and claims priority benefit under 35 U.S.C. § 119 of Japanese patent application 2010-132860, filed Jun. 10, 2010. The entire contents of each of the three mentioned applications are incorporated herein by reference.

BACKGROUND OF THE INVENTION

Field of the Invention

In recent years, photoacoustic tomography, which uses the characteristic of ultrasound waves being less diffusible in a living body than light to calculate an optical characteristic value distribution in the living body at high resolution, has been proposed. In this specification, hereinafter, photoacoustic tomography will be referred to as "PAT". In a measuring apparatus using the principle of PAT, when pulsed light generated from a light source irradiates a living body, it is propagated while diffusing in the living body. An absorber included in biological tissue absorbs the energy of the propagated pulsed light to generate an acoustic wave (the acoustic wave is also called a "photoacoustic wave", and is typically an ultrasound wave). An acoustic wave signal obtained by detecting and signal-processing the acoustic wave is subjected to an analyzing process, so that an optical characteristic distribution, in particular, an optical energy absorption density distribution, in the living body can be obtained.

In PAT, the sound pressure (P) of the acoustic wave obtained from the absorber in the living body by light absorption can be expressed by the following equation (1):

$$P = \Gamma \cdot \mu a \cdot \Phi \qquad \text{Equation (1)}$$

Here, Γ is a Grüneisen coefficient which is an elastic characteristic value, and is obtained by dividing the product of the coefficient of cubic expansion (β) and the square of the sound speed (c) by the specific heat (Cp). μa is the absorption coefficient of the absorber, and Φ is the light amount in a local region (the light amount irradiating the absorber).

In recent years, breast diagnosis has been studied as a possible application of PAT to living bodies. In this specification, use of PAT apparatus for breast diagnosis will be referred to as "photoacoustic mammography" (or "PAM"). A PAM apparatus is an apparatus which images angiogenesis formed around a tumor at the time the tumor is formed, and a region having high absorption coefficient and including the angiogenesis, thereby detecting the tumor position in a breast. To diagnose the entire breast by PAM, measurement is required to be possible in a deep region, even at a depth above 4 to 5 cm below the surface of the patient's body. Although the acoustic wave signal intensity is in proportion to the light amount Φ the beam incident on the biological tissue is diffused, with the result that the light amount reaching the deep portion decreases exponentially with depth. For this reason, to enable depth observation, light preferably irradiates a wide range at as high an irradiation intensity as is permissible for living bodies (the "MPE", or maximum permissible exposure). Therefore, as the light source, a high-output flash lamp excitation solid-state laser is typically used.

The flash lamp excitation solid-state laser has a locally high energy output distribution, the light amount distribution in a beam being less uniform than a semiconductor laser or a He—Ne laser. When a beam at locally high energy density is used, only part of it is at the upper limit of irradiation intensity. Therefore, the light amount distribution of a beam is preferably made uniform using a light modulation member such as a diffusing plate (see U.S. Patent Application Publication No. 2006/0184042).

SUMMARY OF THE INVENTION

In PAM having a breast holding mechanism which fixes an observed portion according to the shape of a breast, unlike X-ray mammography, the following problems arise. In X-ray mammography, since X-rays travel substantially straight in a living body, the X-ray intensity distribution in the living body cannot be affected by the position of the parallel plates of the breast holding mechanism.

On the other hand, in PAM, when a light diffusing plate is installed in a beam propagation path in order to make the light amount distribution in the beam uniform, the outgoing beam diverges increasingly, in accordance with the propagation distance. For this reason, when the distance from the surface of the patient's body to the diffusing plate is different at the time of measurement of an object at plural points, the size of the irradiation region becomes different. As a result, the irradiation intensity at each point is changed according to the breast fixing position, which deteriorates the photoacoustic signal.

The present invention has been made in view of the above problems, and an object of the present invention is to provide a photoacoustic measuring apparatus which can irradiate the surface of a living body uniformly and efficiently.

This invention provides a photoacoustic measuring apparatus comprising:

a light source;

a movable holding unit which holds an object;

a light diffusing unit which fixes the distance between the light diffusing unit and the holding unit and diffuses light incident from the light source; and an acoustic wave obtaining unit which obtains an acoustic wave generated from the object by the light emitted via the holding unit and the light diffusing unit.

According to the photoacoustic measuring apparatus of the present invention, the surface of a living body can be irradiated uniformly and efficiently.

Further features of the present invention will become apparent from the following description of exemplary embodiments with reference to the attached drawings.

DESCRIPTION OF THE EMBODIMENTS

Hereinafter, preferred embodiments of the present invention will be described with reference to the drawings. However, the size, material, shape, and relative arrangements of components described below should be appropriately changed according to the configuration of the particular apparatus to which the present invention is applied and to the actual conditions obtaining, and the scope of the present invention is not intended to be limited to the following description.

A photoacoustic measuring apparatus has a living body holding mechanism which fixes the measured portion of an object. As breast fixing methods in breast diagnosis, a method for fixing the side surfaces of a breast using two parallel plates, a method for entirely pressing and fixing the front surface of a breast, and a method for arcuately fixing a portion around a breast have been proposed. In particular, a breast holding mechanism using a parallel plate has the advantage of being arbitrarily movable according to the size of the patient's breast. In addition, the breast holding mechanism using a parallel plate is adapted to X-ray mammography, and thus has another advantage in that image comparison with X-ray mammography is easy.

When a breast is fixed using a parallel plate in PAM, some light irradiation directions and ultrasound detector arranging directions with respect to the parallel plate can be considered. This will be described with reference to FIGS. 1 to 3. Further, in the description of these, it should be borne in mind that two parallel plates, not shown, which sandwich and hold a breast are present.

Figure 1:
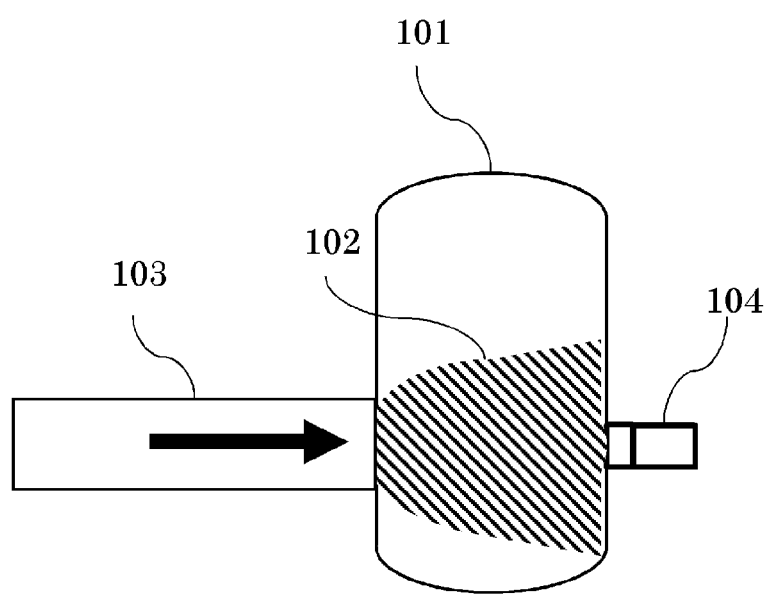
FIG. 1 is a schematic diagram of a front detection type PAT apparatus.
Figure 2:
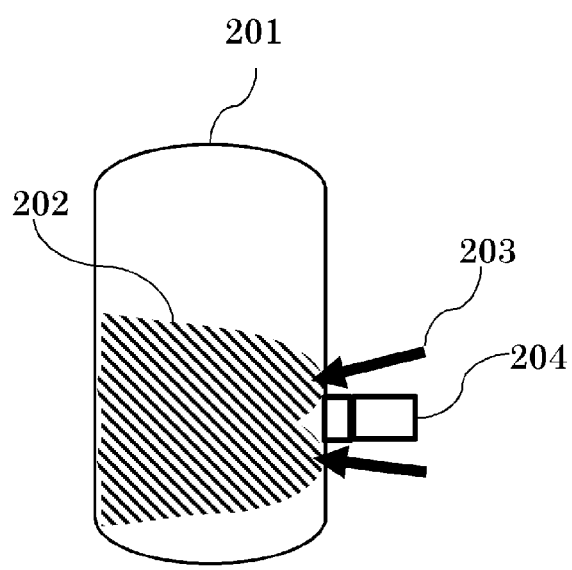
FIG. 2 is a schematic diagram of a rear detection type PAT apparatus.
Figure 3:
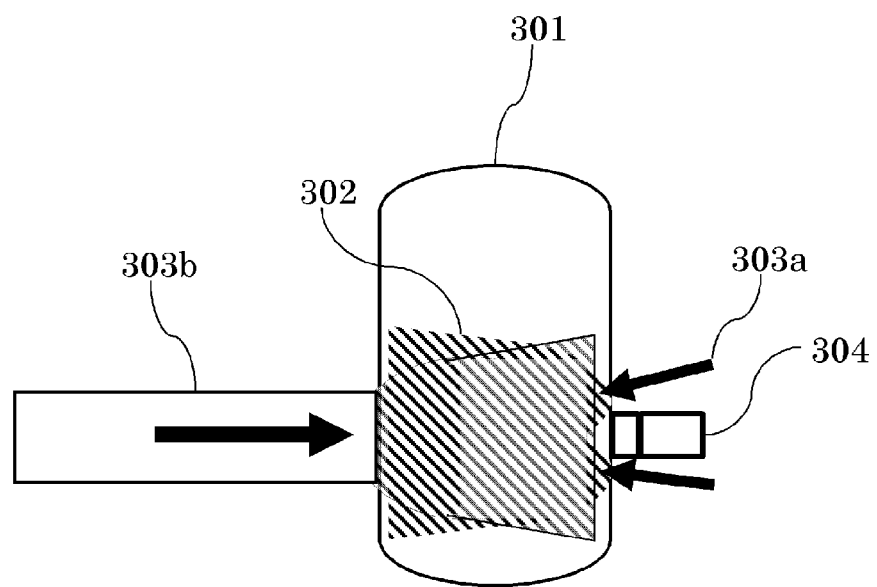
FIG. 3 is a schematic diagram of a both-side (bilateral) irradiation type PAT apparatus.

FIG. 1 shows a front detection type apparatus in which an ultrasound detector 104 is arranged on the opposite side of irradiation light 103 with respect to an object 101. The irradiation light is emitted by diffusion in a living body, as shown in a diffused light area 102. FIG. 2 shows a rear detection type apparatus in which an ultrasound detector 204 is arranged on the same side as irradiation light 203 with respect to an object 201. The irradiation light is emitted, as shown in a diffused light area 202. FIG. 3 shows a bilateral irradiation type apparatus in which irradiation light 303b is emitted from the opposite side of an ultrasound detector 304 with respect to an object 301, and irradiation light 303a is emitted from the same side as the ultrasound detector 304 with respect to the object 301. The irradiation light is emitted, as shown in a diffused light area 302.

In the parallel plates used to sandwich and hold the breast, various movable forms of moving each of the parallel plates on the ultrasound detector side and on the opposite side independently, moving only (either) one of them, and the like can be selected. The movable parallel plates can appropriately press and hold the breast even given the variations that exist among individuals.

In the irradiation used in PAM, the locally high irradiation energy density region can be removed by using a light diffusing mechanism. Further, the irradiation intensity of the entire irradiation region can be made uniform with uniformity according to diffusion angle. The irradiation range of a beam which has passed through the light diffusing mechanism is diverged according to diffusion angle. Here, with the use of the movable parallel plates for fixing the breast, when the light diffusing mechanism is fixed, the distance from the light diffusing mechanism to the parallel plate, that is, the beam propagation distance, is changed with the movement of the plate, so that the irradiation region is changed.

By the way, the permissible light amount in the irradiation onto the surface of a living body is defined according to irradiation energy or irradiation amount per unit area. For this reason, when the irradiation region is varied to increase the irradiation area, the light amount per unit area onto the surface of a living body is decreased. On the other hand, when the irradiation area is decreased, the light amount per unit area onto the surface of a living body is increased, so that the irradiation intensity can be equal to or larger than MPE (maximum permissible exposure). In PAM which requires depth observation, it is preferred that the irradiation intensity be constant within the safe irradiation light amount range equal to or smaller than MPE and be high so that depth observation is enabled. For this reason, the irradiation region is required to be constant regardless of the movement of the movable parallel plate.

Figures 4A, 4B:
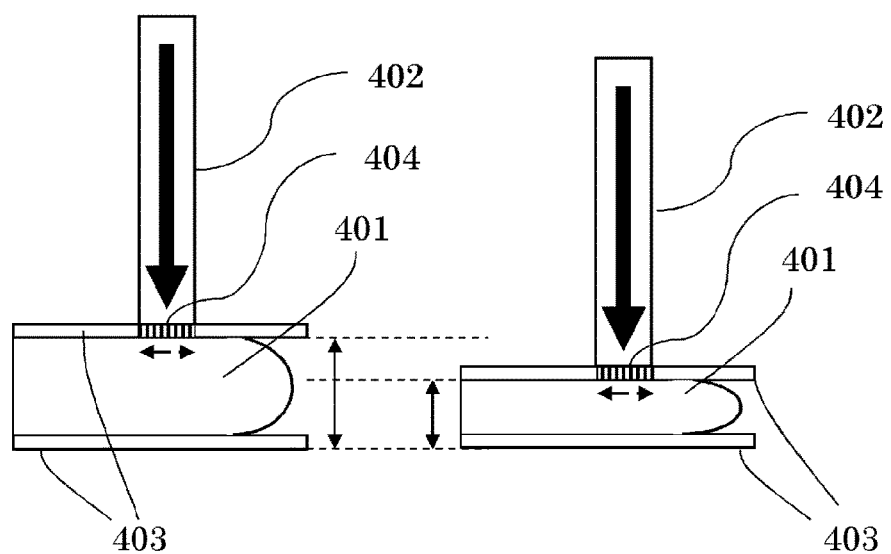
FIGS. 4A and 4B are diagrams each showing an irradiation region when a living body holding mechanism including a diffusing mechanism is provided.

A method for making the irradiation region constant in the present invention will be described below. In FIGS. 4A and 4B, light 402 is emitted from a light source (not shown). In the breast holding mechanism shown in FIGS. 4A and 4B, a light diffusing mechanism 404 is provided to a parallel plate 403 itself. FIGS. 4A and 4B show, in the breast holding mechanism, two types of configurations, in which the interval between the parallel plates is different. As shown in these drawings, the irradiation region formed by the beam via the light diffusing mechanism is not changed, and has a constant area regardless of the interval between the parallel plates 403. Alternatively, even when the movable parallel plate is moved to press and hold the breast, the irradiation region cannot be changed as between before and after movement.

To realize the light diffusing mechanism, there is a method for making the light amount distribution of a beam uniform by providing a surface diffusing mechanism in which the surface shape on the incident side is roughened like ground glass. However, when ground glass is used, much 0-order light is included so that a beam perpendicularly incident upon the substrate is perpendicularly outgoing therefrom. For this reason, to increase the uniformity of the light amount distribution, the use of a holographic diffusing plate in which a micron-level surface structure in surface relief hologram pattern is randomly arranged on the surface of the substrate is effective. The uneven shape of the surface can be pattern-formed by epoxy UV curing. The diffusion angle can be selected according to non-periodic uneven shape, so that the beam can be diffused at high transmissivity without depending on the visible to infrared wavelengths.

In addition, the light diffusing mechanism can also use volume diffusion, in which particles having different refractivities are included in the parallel plate substrate for diffusion control in the parallel plate. In particular, volume diffusion can be done by including titania particles in an acrylic or polycarbonate substrate. The diffusion angle can be increased, not only by including the particles uniformly in the substrate, but also by increasing the amount of particles included from the incident side to the outgoing side to increase the diffusion coefficient. When laser light having high coherence is used, the beam can be locally focused near the surface in the substrate due to refraction on the surface of the substrate. The diffusion is increased gradually, to lower the possibility that the beam might be focused, so that the light can be diffused uniformly.

In this way, the light diffusing mechanism of the parallel plate is referred to as the light diffusing mechanism provided on the surface of the plate or inside the plate. As a result, the entire plate has a diffusion angle defined in a predetermined range. When the diffusion angle is shown as full width at half maximum, the entire light diffusing mechanism (light diffusing unit) of the present invention has a diffusion angle of 0.5☐ or more. The diffusion angle is preferably 1☐ or more, and more preferably is 5☐ or more. Such light diffusing mechanism emits uniform light onto the object.

Figures 5A, 5B:
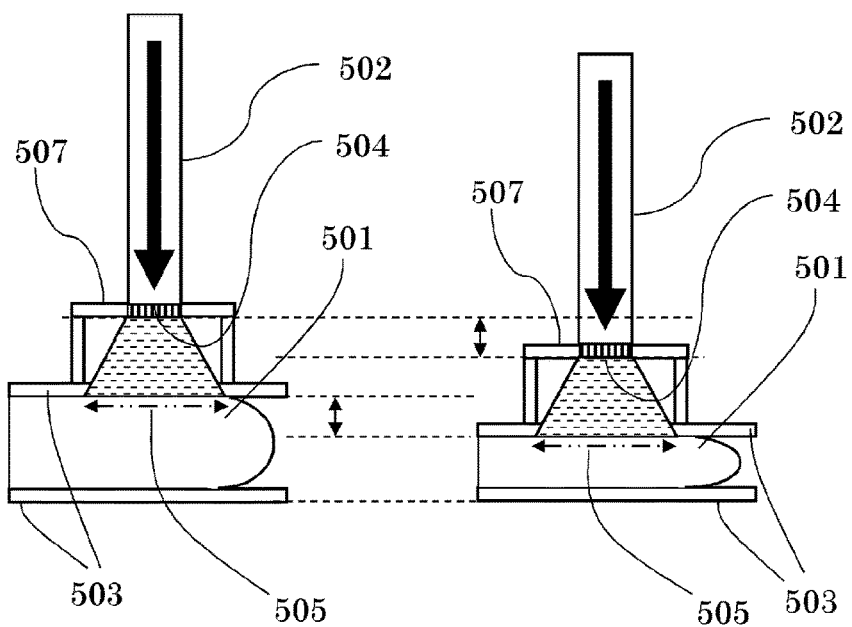
FIGS. 5A and 5B are further diagrams each showing an irradiation region when a living body holding mechanism including a diffusing mechanism is provided.

In addition, as shown in FIGS. 5A and 5B, a jig 507, which is a fixing member which holds the interval between the light diffusing mechanism 504 and parallel plate 503 constant, can be provided. In this case, since the jig having the diffusing mechanism can be moved together according to the movement of the holding mechanism, the irradiation region 505 can be constant. For instance, even when the state of FIG. 5A is changed to the state of FIG. 5B in which the parallel plate is moved in the direction pressing and holding the breast, the irradiation area on the surface of the breast is not changed. In the configuration of FIGS. 5A and 5B, unlike the case in which the light diffusing mechanism is provided on the parallel plate, the surface diffusing mechanism is provided on the light-outgoing side.

However, the light diffusing mechanism 504 may be a member using a volume diffusing mechanism in addition to the member using the surface diffusing mechanism. In addition, when the diffusing mechanism is provided on the surface of the light diffusing mechanism 504 installed in the space in which the light is propagated, the diffusing surface may be the incident side or the outgoing side. However, when laser light that is large in light amount and high in coherence is used, the beam can be locally focused near the surface in the parallel plate by refraction on the surface of the parallel plate. Therefore, in the light diffusing member using a material with low damage resistance, the outgoing side is preferably the diffusing surface.

Figures 6A, 6B:
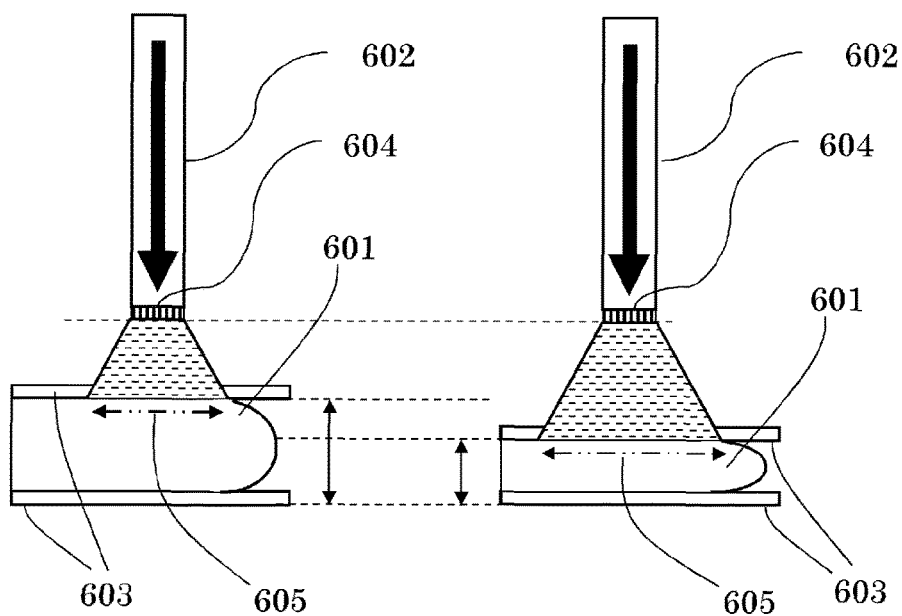
FIGS. 6A and 6b are diagrams each showing the irradiation region of a comparative example in which a diffusing mechanism is fixed.

FIGS. 6A and 6B show the configurations of a comparative example with respect to the forms of FIGS. 5A and 5B. In these configurations, the position of a light diffusing mechanism 604 is fixed, and the distance between the light diffusing mechanism and the plate is increased as the parallel plate is moved in the direction pressing the object. In this case, with the movement of the parallel plate, an irradiation region 605 of the diffused beam is changed (enlarged) from FIG. 6A to FIG. 6B. As a result, the irradiation intensity in the irradiation region is significantly lower than MPE, thereby lowering the measuring efficiency.

First Example

In this example, a configuration example of a front detection type PAT apparatus to which the present invention is applied will be described.

Figure 7:
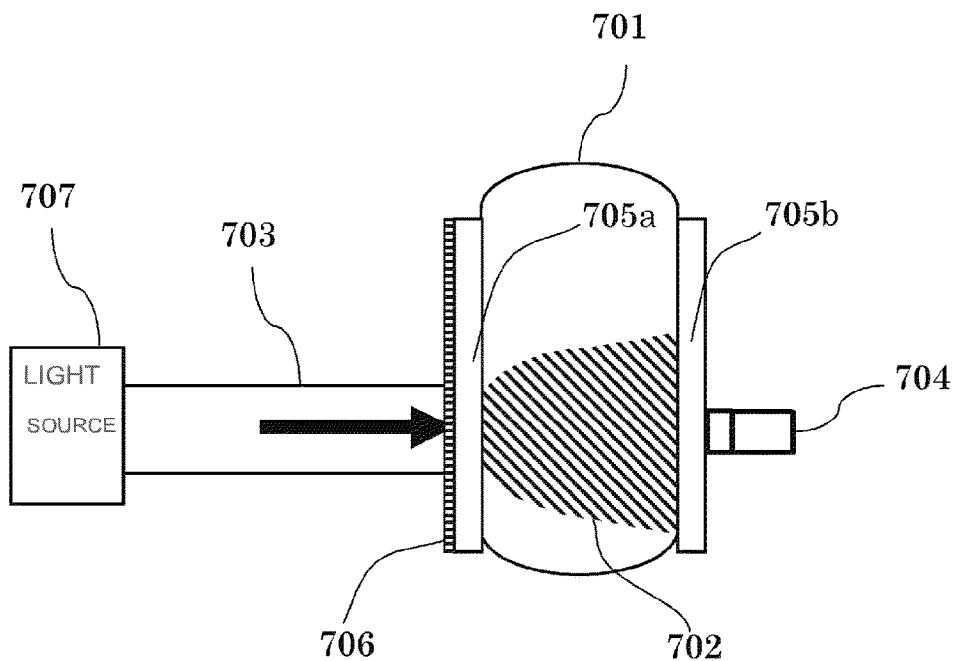
FIG. 7 is a schematic diagram of a front detection type PAT apparatus according to a first example.

As shown in FIG. 7, the front detection type PAT apparatus having planar parallel plates 705a and 705b, an ultrasound detector 704, and a light source 707 which emits irradiation light 703 is prepared for a biological tissue 701 as an object. The emitted light is diffused to irradiate a diffused light area 702. In addition, in this apparatus, the ultrasound detector scans the surface of the plate 705a. The beam on the opposite side is moved with the movement of the ultrasound detector to irradiate the front surface (the left side on the drawing sheet) of the ultrasound detector 704 at all times.

As the light source, a Nd:YAG laser, which is a pulse laser having an oscillation wavelength of 1064 nm, is used. Other than this, the wavelength band from the visible to the infrared region of about 500 nm to 1400 nm can be used. The wavelength varying technique using TI:sa (titanium-sapphire) and OPO (optical parametric generation) used together with the Nd:YAG laser and an alexandrite laser using an alexandrite crystal which oscillates in the wavelength band of about 750 nm can also be used. As the parallel plates 705a and 705b, polymethylpentene having a refractivity of 1.46 is used, the thickness being 10 mm.

In this example, a holographic diffusing mechanism which is the surface diffusing mechanism is provided on the incident side of the plate 705b on the opposite side of the plate 705a on which the ultrasound detector 704 is arranged, that is, on the outside of the plate that does not contact the patient's breast. For that, a sheet 706 having the holographic diffusing mechanism adheres to the parallel plate 705b. Alternatively, the surface of the plate may be directly processed to form the holographic diffusing mechanism. That is, the surface diffusing mechanism may be part of the plate, or may be a member different from the plate. The parallel plate corresponds to the "holding unit" in the embodiments described above, and similarly, the sheet having the holographic diffusing mechanism corresponds to the "light diffusing unit".

The diffused light is absorbed into the biological tissue 701 to generate an ultrasound wave (acoustic wave) by expansion and contraction of the biological tissue. This is obtained by the ultrasound detector 704. The ultrasound detector includes, e.g., a piezoelectric device, and can convert the obtained ultrasound wave to an electric signal which is used for image reconstruction, that is, to produce an image containing information about the biological tissue. The ultrasound detector corresponds to the "acoustic wave obtaining unit" referred to above.

With the use of the PAT apparatus having such configuration, one or both of the parallel plates 705a and 705b are moved according to the size of the breast, to hold the breast for measurement, so that the distance from the light diffusing mechanism to the object is constant. As a result, the variation of the irradiation region by light diffusion can be inhibited, so that irradiation can be performed effectively.

Second Example

In this example, a configuration example of a rear detection type PAT apparatus to which the present invention is applied will be described.

Figure 8:
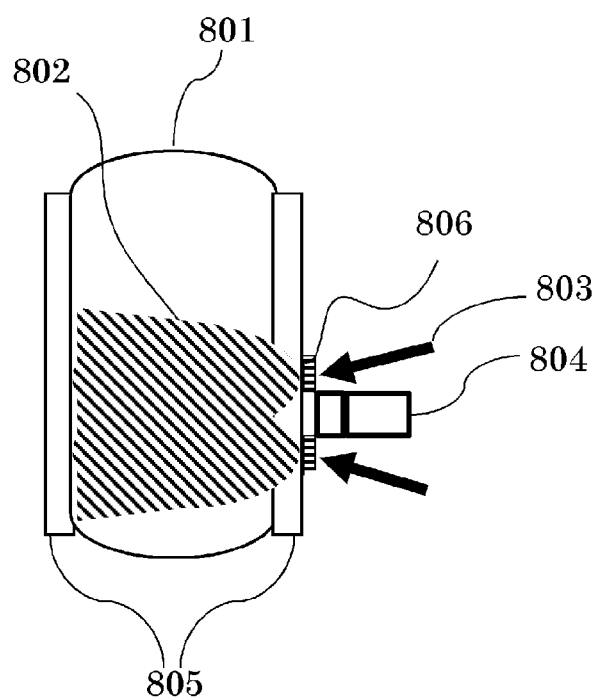
FIG. 8 is a schematic diagram of a rear detection type PAT apparatus according to a second example.

As shown in FIG. 8, the rear detection type PAT apparatus having parallel plates 805, an ultrasound detector 804, and irradiation light 803 of a light source (not shown) is prepared for a biological tissue sample (e.g., a patient's breast) 801. The same light source as the first example can be used. The light emitted from the light source is diffused to irradiate a diffused light area 802.

A film larger than the detector surface and subjected to acoustic matching is fixed on the front surface of the ultrasound detector. The film preferably has higher ultrasound wave transmissivity, and requires light transmissivity. In this example, a polycarbonate film having a thickness of 200 ☐m is used. A unit which integrates the ultrasound detector and the polycarbonate film is contacted with the plate holding the breast via a solution, such as castor oil, which becomes an acoustic matching layer which can easily pass an ultrasound wave therethrough, and is moved in parallel. As the light diffusing mechanism, a surface diffusing mechanism 806 which is the holographic diffusing mechanism is provided on the polycarbonate film. The surface diffusing mechanism is provided on a region other than the contacted portion of the polycarbonate film and the ultrasound detector 804, so that the beam is incident from the region.

In measurement performed using the PAT apparatus having such configuration, even when the parallel plate 805 is moved according to the size of the breast to hold the breast, the distance from the light diffusing mechanism to the object is held constant. As a result, variation of the irradiation region by light diffusion can be inhibited, so that irradiation can be performed effectively.

Although the rear detection type PAT apparatus has been described here, the method of this example is combined with the method of the first example to emit the light from the light source onto the opposite side of the ultrasound detector, so that a both-side irradiation type PAT apparatus can be realized.

In addition, the configuration of this example can also include one plate by eliminating the plate on the opposite side of the ultrasound detector. In that case, the breast is pressingly fixed and held for measurement. This configuration can also inhibit the variation of the irradiation region by diffusion, so that irradiation can be performed effectively. In addition, when the breast is pressingly fixed by an arc member, the present invention is applicable.

Third Example

In this example, a configuration example in which the light diffusing mechanism is realized by volume diffusion in place of surface diffusion used in the above examples will be shown.

Figure 9:
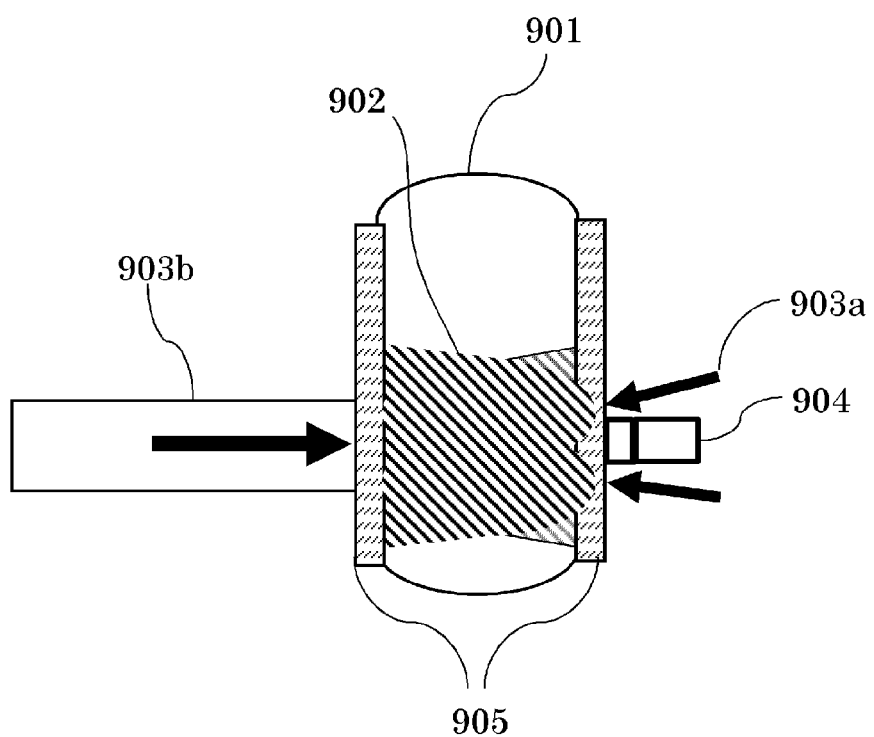
FIG. 9 is a schematic diagram of a bilateral irradiation type PAT apparatus performing volume diffusion according to a third example.

FIG. 9 shows the configuration of the PAT apparatus of this example. Here, the polycarbonate film which provides surface diffusion to the front surface of the ultrasound detector, as shown in the above example, is not necessary. A biological tissue 901 such as a breast is the object, and is sandwiched and held between parallel plates 905. Irradiation lights 903a and 903b led by an optical system from a light source (not shown) irradiate the object and are diffused onto a diffused light area 902. An ultrasound detector 904 detects an acoustic wave generated from the patient.

In this example, to adjust the refractivity in the polymethylpentene resin which is the material of the parallel plates 905, titania particles are included. Two titania inclusion methods in which titania particles are uniformly included in the plates, and in which the rate of titania particles included is graduated, so as to gradually increase the diffusion effect from the incident side to the outgoing side of the beam, are prepared.

Whichever of these two types of plates is used, the parallel plate 905 is moved according to the size of the breast using the PAT apparatus having such configuration to hold the breast for measurement, the distance from the light diffusing mechanism to the object can be held constant. As a result, variation of the irradiation region by light diffusion can be inhibited, so that irradiation can be performed effectively. Between these two types of plates, the one in which the amount of titania is gradually increased from the incident side, may be preferable in that the beam is prevented from being locally focused near the surface by refraction.

As another form of this example, a configuration example in which the diffusing mechanism moving with the breast holding mechanism is provided may be adopted. In this case, the interval between the parallel plates as the breast holding mechanism is changed depending on the size of the breast. The movable parallel plate is coupled to the member having the diffusing mechanism to hold the distance between the plate and the diffusing member. As in the first example, since the beam on the opposite side is in-plane operated with the ultrasound detector at the time of acoustic wave signal measurement, the diffusing member has sufficiently large vertical and horizontal sizes, so that the beam can be emitted via the diffusing member at all times.

By such configuration, the variation of the irradiation region by diffusion can be inhibited, so that irradiation can be performed effectively.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A photoacoustic measuring apparatus comprising:
   a holding unit configured to hold an object;
   a light emitting unit configured to emit light generated by a light source;
   a diffusing plate configured to diffuse the light emitted from the light emitting unit to irradiate the object with the diffused light; and
   an acoustic wave obtaining unit configured to obtain an acoustic wave generated from the object by the irradiation,
   wherein the holding unit and the diffusing plate are integrated,
   wherein the photoacoustic measuring apparatus is configured such that the light entering the diffusing plate from a first principal surface of the diffusing plate exits from a second principal surface of the diffusing plate and irradiates the object,
   wherein the second principal surface is opposed to the first principal surface.

2. The photoacoustic measuring apparatus according to claim 1, wherein an area of an irradiation region on a surface of the object contacting the holding unit is kept constant even when the holding unit moves.

3. The photoacoustic measuring apparatus according to claim 1, wherein the diffusing plate is provided with a surface diffusing mechanism on a light outgoing side.

4. The photoacoustic measuring apparatus according to claim 1, wherein the diffusing plate comprises a volume diffusing mechanism.

5. A photoacoustic measuring apparatus comprising:
   a holding unit configured to hold an object;
   a light emitting unit configured to emit light generated by a light source;
   a diffusing plate configured to diffuse the light emitted from the light emitting unit to irradiate the object with the diffused light; and
   an acoustic wave obtaining unit configured to obtain an acoustic wave generated from the object by the irradiation,
   wherein the holding unit and the diffusing plate are integrated,
   wherein the photoacoustic measuring apparatus is configured such that the light entering the diffusing plate from a first principal surface of the diffusing plate exits from a second principal surface of the diffusing plate and irradiates the object, and wherein a diffusion coefficient inside the diffusing plate increases with distance from the first principal surface.

6. The photoacoustic measuring apparatus according to claim 5, wherein an area of an irradiation region on a surface of the object contacting the holding unit is kept constant even when the holding unit moves.

7. The photoacoustic measuring apparatus according to claim 5, wherein the diffusing plate is provided with a surface diffusing mechanism on a light outgoing side.

8. The photoacoustic measuring apparatus according to claim 5, wherein the diffusing plate comprises a volume diffusing mechanism.

* * * * *